United States Patent
Hawkes

(10) Patent No.: US 11,170,162 B2
(45) Date of Patent: *Nov. 9, 2021

(54) ANALYSIS SYSTEM

(71) Applicant: Michael Garnet Hawkes, Delray Beach, FL (US)

(72) Inventor: Michael Garnet Hawkes, Delray Beach, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 17/027,518

(22) Filed: Sep. 21, 2020

(65) Prior Publication Data

US 2021/0073462 A1 Mar. 11, 2021

Related U.S. Application Data

(63) Continuation of application No. 16/352,823, filed on Mar. 14, 2019, now Pat. No. 10,783,323.

(51) Int. Cl.
*G06F 17/00* (2019.01)
*G06F 40/174* (2020.01)
*G06K 9/00* (2006.01)
*G06K 9/46* (2006.01)
*G16H 20/10* (2018.01)

(52) U.S. Cl.
CPC ....... *G06F 40/174* (2020.01); *G06K 9/00442* (2013.01); *G06K 9/00852* (2013.01); *G06K 9/46* (2013.01); *G16H 20/10* (2018.01); *G06K 2209/01* (2013.01)

(58) Field of Classification Search
CPC .... G06F 40/174; G06K 9/00442; G06K 9/46; G06K 9/00852; G06K 2209/01; G06K 9/00429; G16H 20/10; G16H 10/60
See application file for complete search history.

(56) References Cited

U.S. PATENT DOCUMENTS

| | | | | |
|---|---|---|---|---|
| 5,134,669 A * | 7/1992 | Keogh | ............... | G06K 9/2018 382/318 |
| 5,402,504 A * | 3/1995 | Bloomberg | ........ | G06K 9/00456 382/175 |
| 5,459,796 A * | 10/1995 | Boyer | ............... | G06F 3/04883 382/187 |
| 5,923,792 A * | 7/1999 | Shyu | ............... | G06K 9/033 382/309 |
| 6,468,084 B1 * | 10/2002 | MacMillan | ............ | G09B 5/04 434/156 |
| 6,989,822 B2 * | 1/2006 | Pettiross | ............... | G06F 3/0236 345/169 |
| 7,039,234 B2 * | 5/2006 | Geidl | ................... | G06F 40/166 382/187 |

(Continued)

*Primary Examiner* — Hassan Mrabi
(74) *Attorney, Agent, or Firm* — The Law Firm of AQ Basit

(57) ABSTRACT

An electronic communications method includes receiving, by a computing device, electronic information, with the electronic information including handwritten text. The electronic communications method includes analyzing, by the computing device, the electronic information, with the analyzing includes analyzing the handwritten text. The electronic communications method includes generating printed text based on analyzing the handwritten text. The electronic communications method includes generating a converted document with the printed text based on the electronic information.

20 Claims, 15 Drawing Sheets

Prescription 100

(56) References Cited

U.S. PATENT DOCUMENTS

| | | | | |
|---|---|---|---|---|
| 7,249,320 | B2* | 7/2007 | Simmons | G06F 40/103 715/255 |
| 7,551,312 | B1* | 6/2009 | Hull | G06K 15/02 358/1.15 |
| 7,774,504 | B2* | 8/2010 | Chene | G06Q 40/00 709/246 |
| 8,170,338 | B2* | 5/2012 | Okita | H04N 1/387 382/179 |
| 8,438,489 | B2* | 5/2013 | Barthelmess | G06F 40/171 715/751 |
| 8,768,836 | B1* | 7/2014 | Acharya | G06F 40/174 705/42 |
| 9,213,970 | B1* | 12/2015 | Felse | H04N 1/0032 |
| 9,252,962 | B1* | 2/2016 | Valeti | G06Q 10/101 |
| 2002/0051262 | A1* | 5/2002 | Nuttall | H04N 1/00392 358/537 |
| 2002/0102022 | A1* | 8/2002 | Ma | G06K 9/00456 382/170 |
| 2002/0107885 | A1* | 8/2002 | Brooks | G06F 40/174 715/224 |
| 2003/0004991 | A1* | 1/2003 | Keskar | G06K 9/2054 715/230 |
| 2003/0016873 | A1* | 1/2003 | Nagel | G06K 9/222 382/228 |
| 2003/0071850 | A1* | 4/2003 | Geidl | G06F 3/04883 715/781 |
| 2003/0142106 | A1* | 7/2003 | Saund | G06K 9/00463 345/582 |
| 2003/0142112 | A1* | 7/2003 | Saund | G06K 9/00463 345/619 |
| 2003/0214531 | A1* | 11/2003 | Chambers | G06F 40/171 715/764 |
| 2003/0215142 | A1* | 11/2003 | Gounares | G06F 3/0481 382/190 |
| 2004/0085301 | A1* | 5/2004 | Furukawa | G06K 9/222 345/179 |
| 2004/0194029 | A1* | 9/2004 | Altman | G06F 40/166 715/255 |
| 2004/0196313 | A1* | 10/2004 | Wynn | G06F 40/171 715/779 |
| 2004/0236710 | A1* | 11/2004 | Clary | G06F 40/174 706/46 |
| 2005/0041266 | A1* | 2/2005 | Silverbrook | H04M 1/21 358/1.15 |
| 2005/0099398 | A1* | 5/2005 | Garside | G06F 3/04883 345/173 |
| 2006/0050969 | A1* | 3/2006 | Shilman | G06F 40/171 382/224 |
| 2006/0062459 | A1* | 3/2006 | Saito | G06K 9/6835 382/181 |
| 2006/0159345 | A1* | 7/2006 | Clary | G06K 9/2063 382/186 |
| 2006/0209040 | A1* | 9/2006 | Garside | G06F 3/04162 345/173 |
| 2006/0221064 | A1* | 10/2006 | Sawada | G06F 40/171 345/173 |
| 2006/0242608 | A1* | 10/2006 | Garside | G06K 9/00436 715/864 |
| 2007/0086032 | A1* | 4/2007 | Gonzalez | G06F 3/03545 358/1.12 |
| 2007/0195370 | A1* | 8/2007 | Suga | G06F 40/174 358/1.18 |
| 2008/0049258 | A1* | 2/2008 | Moyo | G06F 3/0321 358/3.28 |
| 2008/0181501 | A1* | 7/2008 | Faraboschi | G06F 40/174 382/179 |
| 2008/0195965 | A1* | 8/2008 | Pomerantz | G06F 21/604 715/780 |
| 2009/0161958 | A1* | 6/2009 | Markiewicz | G06K 9/00436 382/186 |
| 2010/0238195 | A1* | 9/2010 | McGee | G06F 3/0483 345/634 |
| 2011/0206268 | A1* | 8/2011 | Faulkner | G06K 9/036 382/140 |
| 2011/0255107 | A1* | 10/2011 | Blau | G06F 40/174 358/1.11 |
| 2012/0163718 | A1* | 6/2012 | Reddy | G06K 9/2054 382/176 |
| 2013/0205189 | A1* | 8/2013 | DiPierro | G06F 3/0483 715/224 |
| 2014/0022184 | A1* | 1/2014 | Bathiche | G06F 3/04883 345/173 |
| 2014/0046841 | A1* | 2/2014 | Gauvin | G06Q 40/02 705/43 |
| 2014/0236790 | A1* | 8/2014 | Smith | G06Q 40/02 705/35 |
| 2014/0278466 | A1* | 9/2014 | Simmons | G16H 20/10 705/2 |
| 2014/0346096 | A1* | 11/2014 | Felse | B07C 3/10 209/584 |
| 2014/0350718 | A1* | 11/2014 | Felse | B07C 3/12 700/225 |
| 2014/0351159 | A1* | 11/2014 | Felse | G06Q 10/083 705/330 |
| 2014/0351160 | A1* | 11/2014 | Felse | G06Q 10/083 705/330 |
| 2014/0351161 | A1* | 11/2014 | Felse | G06Q 10/083 705/330 |
| 2014/0372266 | A1* | 12/2014 | Tatham | G06Q 20/042 705/33 |
| 2014/0372296 | A1* | 12/2014 | Tatham | G06Q 20/0425 705/40 |
| 2015/0067485 | A1* | 3/2015 | Kim | G06F 40/151 715/256 |
| 2015/0067504 | A1* | 3/2015 | Kim | G06F 3/0485 715/708 |
| 2017/0060406 | A1* | 3/2017 | Rucine | G06F 3/0484 |
| 2017/0083499 | A1* | 3/2017 | VanBlon | G06F 3/04883 |
| 2017/0091153 | A1* | 3/2017 | Thimbleby | G06F 3/04842 |
| 2017/0091873 | A1* | 3/2017 | Cole | G06Q 20/10 |
| 2017/0199660 | A1* | 7/2017 | Guiavarc'h | G06K 9/00429 |
| 2018/0114059 | A1* | 4/2018 | Ric | G06K 9/00865 |
| 2018/0137349 | A1* | 5/2018 | Such | G06N 3/0454 |
| 2018/0260376 | A1* | 9/2018 | Newby | G06F 40/143 |
| 2018/0285321 | A1* | 10/2018 | Antony | G06K 9/6892 |
| 2018/0341635 | A1* | 11/2018 | Brugler | G06F 3/03545 |
| 2018/0349692 | A1* | 12/2018 | Dixon | G06K 9/222 |
| 2019/0026019 | A1* | 1/2019 | Guiavarc'h | G06F 3/04886 |
| 2019/0064938 | A1* | 2/2019 | Klein | G06F 40/171 |
| 2019/0129921 | A1* | 5/2019 | Calcaterra | G06F 40/103 |

* cited by examiner

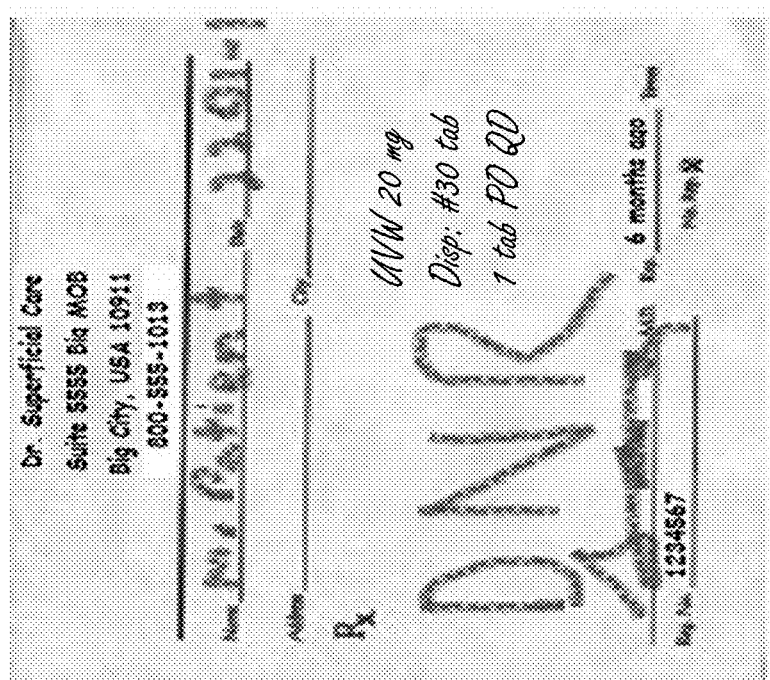
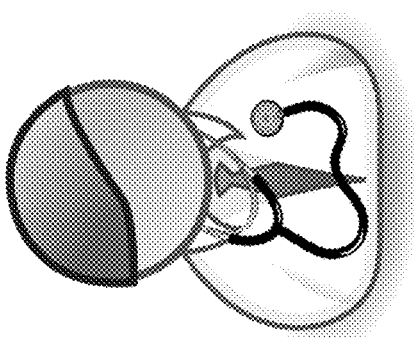
Prescription 100
Doctor Care writes Prescription
FIG. 1A

| ID (602) | LOCATION (604) | HANDWRITING STYLE (606) | DOCTOR (608) | TEXT (610) |
|---|---|---|---|---|
| X889 | Miami | CL | Smith | XY14 |
| 012W | New York | STX | Patel | IU22 |
| 884A | San Diego | TU2 | Chang | 88PI |
| ● | ● | ● | ● | ● |
| ● | ● | ● | ● | ● |

FIG. 6

ANALYSIS SYSTEM

BACKGROUND

A handwritten document may have text and/or other markings that may not be legible when read by a person. In various situations, illegible text can result in improper medical advice or drugs being given to patients. There is currently no system that provides for an effective way to electronically analyze handwritten text.

BRIEF DESCRIPTION OF DRAWINGS

FIGS. 1A-1B are diagrams of an example environment in which systems and/or methods described herein may be implemented;

FIG. 6 is an example database structure for information associated with communication features.

DETAILED DESCRIPTION OF PREFERRED EMBODIMENTS

Figure 1B:
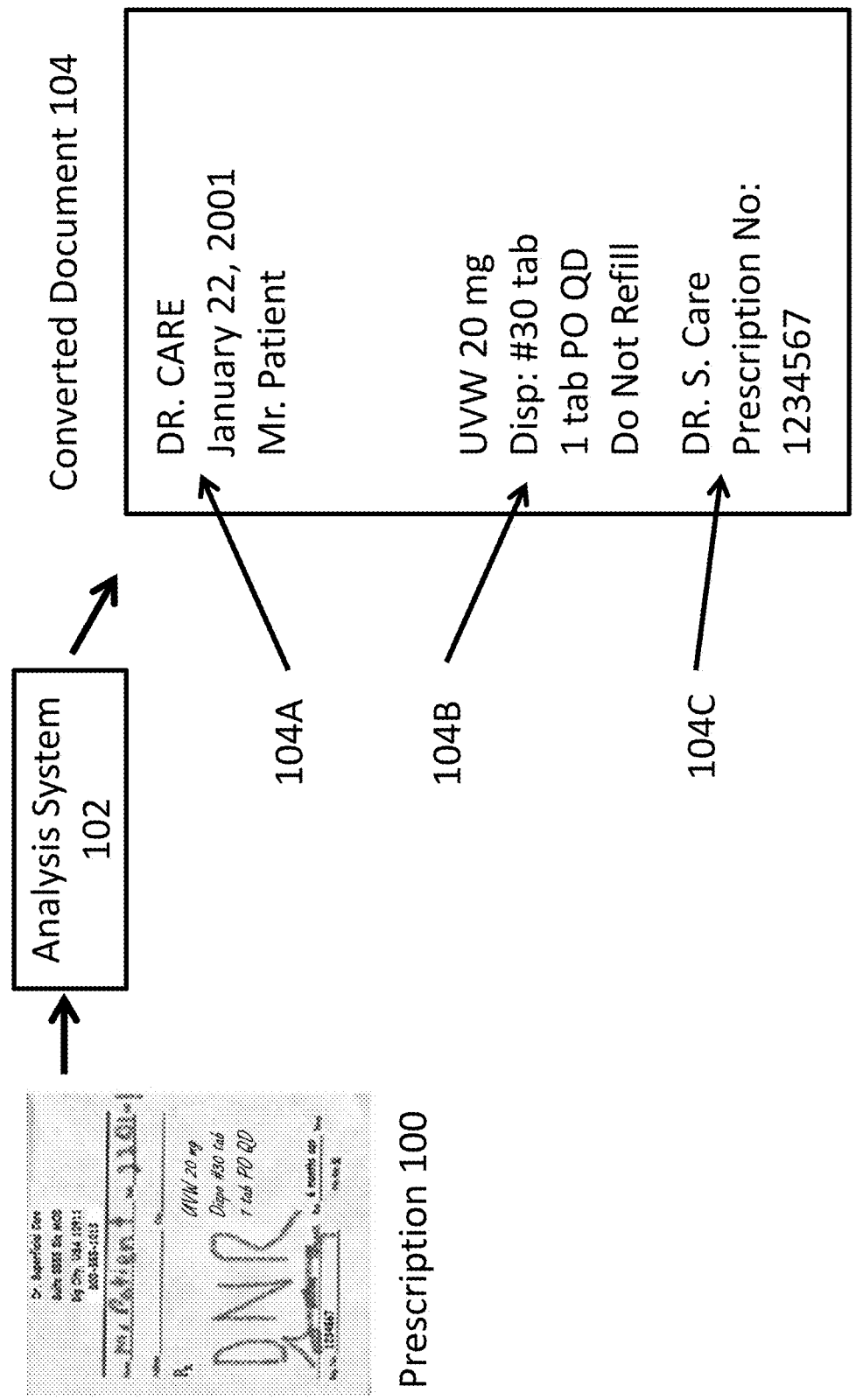

The following detailed description refers to the accompanying drawings. The same reference numbers in different drawings may identify the same or similar elements.

Systems, devices, and/or methods described herein may allow for a user, using a computing device (e.g., smartphone, laptop, etc.) to receive one or more original documents, electronic or non-electronic, and, using an electronic application associated with the computing device, analyze text within the one or more documents. In embodiments, the original document may include handwritten text that may or may not be legible for reading by a person. In embodiments, the analysis of the text includes electronically analyzing one or more features of the text and then converting the text into electronic text as part of a converted document. In embodiments, the converted electronic text may be displayed on an electronic screen and/or used to generate a non-electronic document (e.g., a printed document on paper). In embodiments, the converted document, whether in electronic or non-electronic form, may be reviewed by an individual (e.g., a pharmacist) to then conduct further activities (e.g., dispensing of drugs). In embodiments, the converted text (e.g., converted electronic text) may now all be legible for reading and/or viewing by a person.

In embodiments, the electronic analysis of the text may include (i) analyzing electronic information from previous original or converted documents, (ii) analyzing geographic information provided in the original document, (iii) analyzing one or more individuals' names associated with the original document, (iv) analyzing location of each text within the original document, (v) analyzing lines, curves, and other features of the text in the original document, (vi) analyzing conjoined words and/or letters, (vii) analyzing symbols in the original document, and (viii) analyzing signatures in the original document.

In embodiments, the electronic analysis of the text may be conducted by an electronic application that can be downloaded and/or saved on an electronic device (e.g., a smartphone, a laptop, a desktop, a tablet, etc.). In embodiments, the electronic application may electronically communicate with one or more other computing devices. In embodiments, the other computing devices may be part of the same electronic network as the electronic device or may be part of another electronic network. In embodiments, the other computing devices may electronically communicate with the electronic device via a local wireless or wired electronic connection. In embodiments, the one or more other computing devices may store electronic information in one or more databases. In embodiments, the electronic device may retrieve previous original or converted documents from an electronic cloud computing system.

Accordingly, by using the systems, methods, and/or processes described in the following figures, a user may analyze non-legible and/or legible text in the original document and convert handwritten information in the original document into converted electronic text that, in graphical or printed form, is legible for reading by a person. In embodiments, the converted electronic text may then be approved by an individual, such as a pharmacist, doctor, etc., for a particular action (e.g., conduct a medical procedure, provide medicines, drugs, etc.).

FIGS. 1A-1B describe one or more example processes for electronically converting text, numbers, and/or symbols from an original document into converted electronic text in a converted document. In this non-limiting example, Doctor Care decides to write a prescription 100, as shown in FIG. 1A. As shown in FIG. 1A, prescription 100 includes Doctor Care's name, address, phone number. In addition, prescription 100 includes printed areas for locations that allows Doctor Care to write a patients name ("Mr. Patient") and a date ("22 01-1"). Prescription 100 also includes a printed (i.e., a non-handwritten) symbol Rx and an area that allows for Doctor Care to write medical information about the prescribed drug. As shown in FIG. 1A, Doctor Care has written "UVW 20 mg, Disp (dispense): #30 tab 1 tab PO QD" and "DNR." Accordingly, Doctor Care then gives prescription 100 to Mr. Patient who decides to go to this pharmacy to obtain the medication, UVW.

Once Mr. Patient arrives at the pharmacy, he provides prescription 100 to a pharmacy technician working at the pharmacy who takes prescription 100 from Mr. Patient. As shown in FIG. 1B, prescription 100 is analyzed by analysis system 102. Analysis system 102 may retrieve the information from prescription 100 by the pharmacy technician taking prescription 100 and having it scanned by a scanning device, and with the scanned electronic document being stored on a computing device at the pharmacy. Analysis system 102 may be an electronic application or software that is also downloaded onto the computing device at the pharmacy. In other examples, an electronic image by camera on a tablet or smartphone may be taken of prescription 100 and analysis system 102 may be an electronic application or software downloaded on the tablet or smartphone that may receive the electronic image. Thus, as shown in FIG. 1B, the handwritten information in prescription 100 has been converted to printed form. The converted document also includes the original printed information from prescription 100. The converted document is then reviewed by a pharmacist who dispenses the drug to Mr. Patient. While a document is shown in FIG. 1B, analysis system 102 may also generate audio generated signs that indicate what was written in prescription 100. The information from prescription 100 and the converted information may be stored by a computing device (not shown in FIG. 1A or 1B) so that future prescriptions can be analyzed based on the stored information from prescription 100. The patient's name may not be stored.

Figure 2:
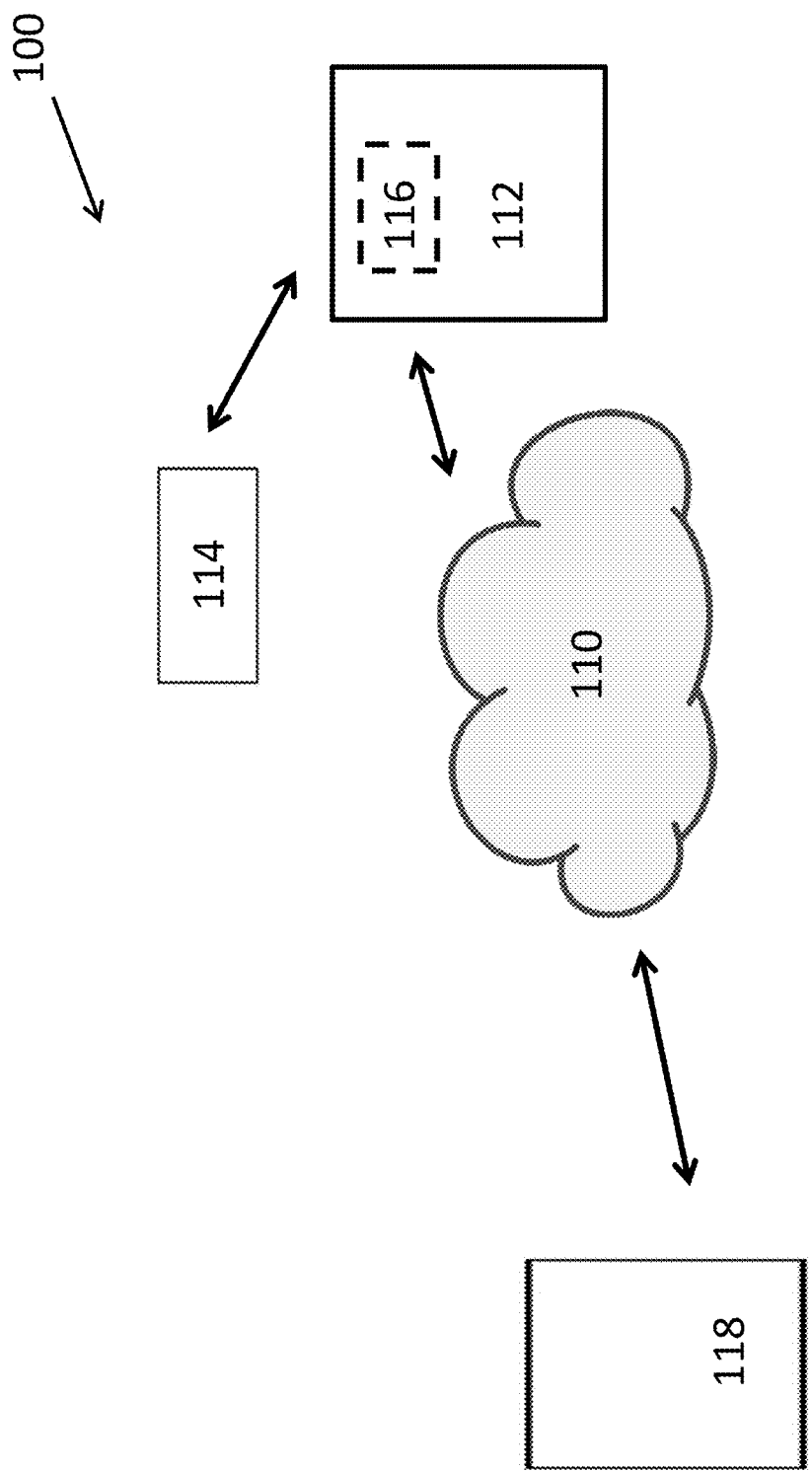
FIG. 2 is a diagram of a network environment.

FIG. 2 is a diagram of example environment 100 in which systems, devices, and/or methods described herein may be implemented. FIG. 2 shows network 110, user device 112, user device 114, electronic application 116, and server 118.

Network 110 may include a local area network (LAN), wide area network (WAN), a metropolitan network (MAN), a telephone network (e.g., the Public Switched Telephone Network (PSTN)), a Wireless Local Area Networking (WLAN), a WiFi, a hotspot, a Light fidelity (LiFi), a Worldwide Interoperability for Microware Access (WiMax), an ad hoc network, an intranet, the Internet, a satellite network, a GPS network, a fiber optic-based network, and/or combination of these or other types of networks. Additionally, or alternatively, network 110 may include a cellular network, a public land mobile network (PLMN), a second generation (2G) network, a third generation (3G) network, a fourth generation (4G) network, a fifth generation (5G) network, and/or another network. In embodiments, network 110 may allow for devices describe any of the described figures to electronically communicate (e.g., using emails, electronic signals, URL links, web links, electronic bits, fiber optic signals, wireless signals, wired signals, etc.) with each other so as to send and receive various types of electronic communications.

User device 112 and/or 114 may include any computation or communications device that is capable of communicating with a network (e.g., network 110). For example, user device 112 and/or user device 114 may include a radiotelephone, a personal communications system (PCS) terminal (e.g., that may combine a cellular radiotelephone with data processing and data communications capabilities), a personal digital assistant (PDA) (e.g., that can include a radiotelephone, a pager, Internet/intranet access, etc.), a smart phone, a scanning device, a desktop computer, a laptop computer, a tablet computer, a camera, a personal gaming system, a television, a set top box, a digital video recorder (DVR), a digital audio recorder (DUR), a digital watch, a digital glass, or another type of computation or communications device.

User device 112 and/or 114 may receive and/or display content. The content may include objects, data, images, audio, video, text, files, and/or links to files accessible via one or more networks. Content may include a media stream, which may refer to a stream of content that includes video content (e.g., a video stream), audio content (e.g., an audio stream), and/or textual content (e.g., a textual stream). In embodiments, an electronic application may use an electronic graphical user interface to display content and/or information via user device 112 and/or 114. User device 112 and/or 114 may have a touch screen, mouse, and/or a keyboard that allows a user to electronically interact with an electronic application. In embodiments, a user may swipe, press, or touch user device 112 and/or 114 in such a manner that one or more electronic actions will be initiated by user device 112 and/or 114 via an electronic application.

User device 112 and/or 114 may include a variety of applications, such as, for example, a conversion application, an e-mail application, a telephone application, a camera application, a video application, a multi-media application, a music player application, a visual voice mail application, a contacts application, a data organizer application, a calendar application, an instant messaging application, a texting application, a web browsing application, a blogging application, and/or other types of applications (e.g., a word processing application, a spreadsheet application, etc.).

Electronic application 116 may be capable of interacting with user device 112, user device 114, server 118, and/or network 110 to automatically and electronically analyze printed and handwritten information in a document and convert the information (converted information) into electronic printed information which can then be printed on paper, viewed on an electronic screen, and/or generate audible sounds based on the converted information. In embodiments, electronic application 116 may generate graphical and alphanumeric features based on electronic communications and transactions associated with the document with the printed and handwritten information. In embodiments, electronic application 116 may interact with other electronic applications (e.g., associated with server 118). In embodiments, electronic application 116 may interact with application programming interfaces (APIs) to obtain electronic information from other electronic applications. In embodiments, electronic application 116 may be electronically configured to show photos, video, text, icons, graphical images, buttons, emojis, and/or any other electronic information. While FIG. 2 shows electronic application 116 on user device 112, electronic application 116 can also be stored, completely or partially, on user device 114, and/or server 118.

Server 118 may include one or computational or communication devices that gather, process, store, and/or provide information relating to one or more web pages or electronic pages that electronically display electronic content (e.g., advertisements, posts, messages, video content) associated with the one or more services.

While FIG. 2 shows electronic application 116, there may be multiple different types of electronic applications 116 that each has their own server(s) that are similar to server 118.

Figure 3:
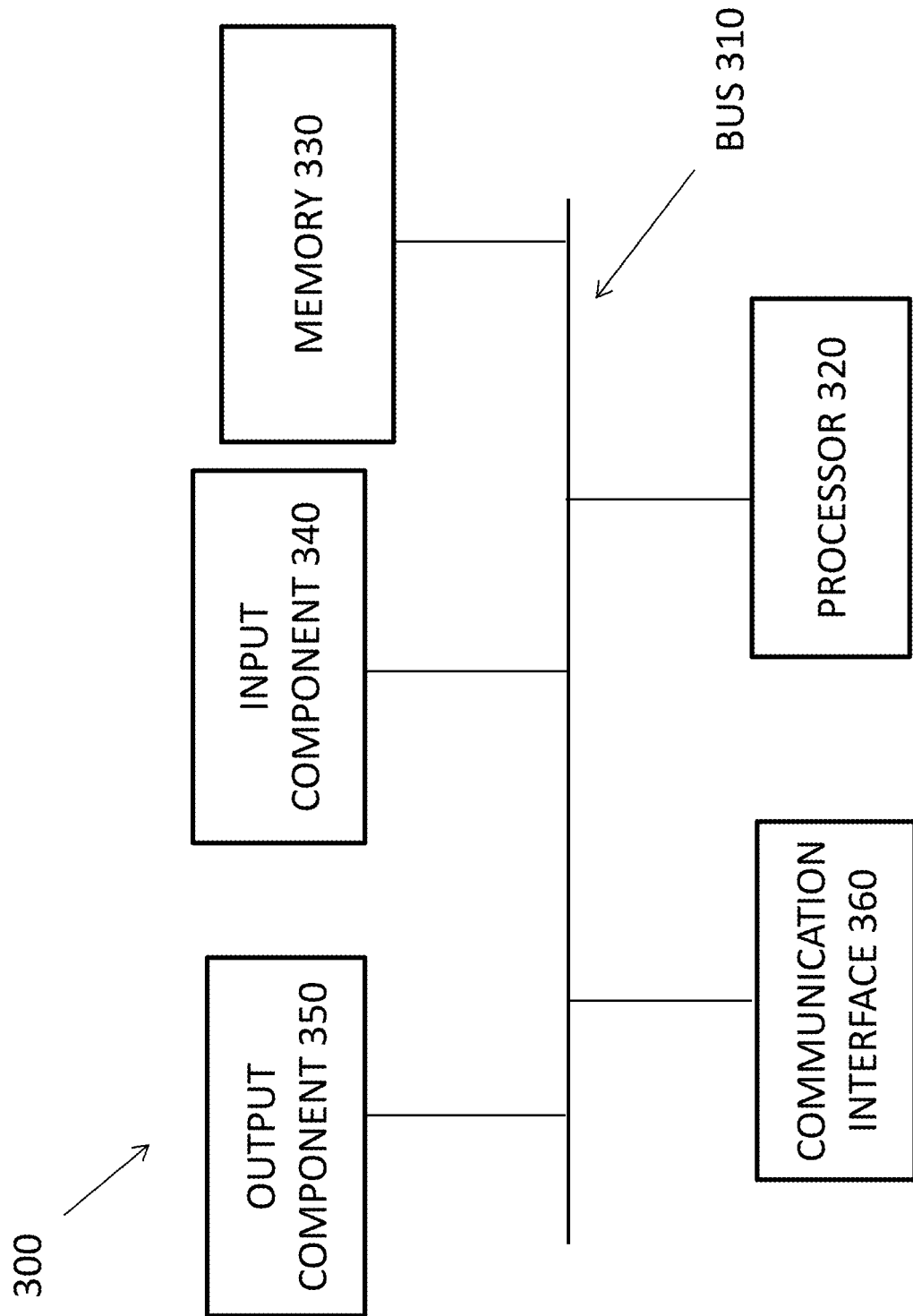
FIG. 3 is a diagram of an example computing device.

FIG. 3 is a diagram of example components of a device 300. Device 300 may correspond to user device 112, user device 114, and server 118. Alternatively, or additionally, user device 112, user device 114, and server 118 may include one or more devices 300 and/or one or more components of device 300.

As shown in FIG. 3, device 300 may include a bus 310, a processor 320, a memory 330, an input component 340, an output component 350, and a communications interface 360. In other implementations, device 300 may contain fewer components, additional components, different components, or differently arranged components than depicted in FIG. 3. Additionally, or alternatively, one or more components of device 300 may perform one or more tasks described as being performed by one or more other components of device 300.

Bus 310 may include a path that permits communications among the components of device 300. Processor 320 may include one or more processors, microprocessors, or processing logic (e.g., a field programmable gate array (FPGA) or an application specific integrated circuit (ASIC)) that interprets and executes instructions. Memory 330 may include any type of dynamic storage device that stores information and instructions, for execution by processor 320, and/or any type of non-volatile storage device that stores information for use by processor 320. Input component 340 may include a mechanism that permits a user to input information to device 300, such as a keyboard, a keypad, a button, a switch, voice command, etc. Output component 350 may include a mechanism that outputs information to the user, such as a display, a speaker, one or more light emitting diodes (LEDs), etc.

Communications interface 360 may include any transceiver-like mechanism that enables device 300 to communicate with other devices and/or systems. For example, communications interface 360 may include an Ethernet interface, an optical interface, a coaxial interface, a wireless interface, or the like.

In another implementation, communications interface 360 may include, for example, a transmitter that may convert baseband signals from processor 320 to radio frequency (RF) signals and/or a receiver that may convert RF signals to baseband signals. Alternatively, communications interface 360 may include a transceiver to perform functions of both a transmitter and a receiver of wireless communications (e.g., radio frequency, infrared, visual optics, etc.), wired communications (e.g., conductive wire, twisted pair cable, coaxial cable, transmission line, fiber optic cable, waveguide, etc.), or a combination of wireless and wired communications.

Communications interface 360 may connect to an antenna assembly (not shown in FIG. 3) for transmission and/or reception of the RF signals. The antenna assembly may include one or more antennas to transmit and/or receive RF signals over the air. The antenna assembly may, for example, receive RF signals from communications interface 360 and transmit the RF signals over the air, and receive RF signals over the air and provide the RF signals to communications interface 360. In one implementation, for example, communications interface 360 may communicate with network 110.

As will be described in detail below, device 300 may perform certain operations. Device 300 may perform these operations in response to processor 320 executing software instructions (e.g., computer program(s)) contained in a computer-readable medium, such as memory 330, a secondary storage device (e.g., hard disk, CD-ROM, etc.), or other forms of RAM or ROM. A computer-readable medium may be defined as a non-transitory memory device. A memory device may include space within a single physical memory device or spread across multiple physical memory devices. The software instructions may be read into memory 330 from another computer-readable medium or from another device. The software instructions contained in memory 330 may cause processor 320 to perform processes described herein. Alternatively, hardwired circuitry may be used in place of or in combination with software instructions to implement processes described herein. Thus, implementations described herein are not limited to any specific combination of hardware circuitry and software.

Figure 4:
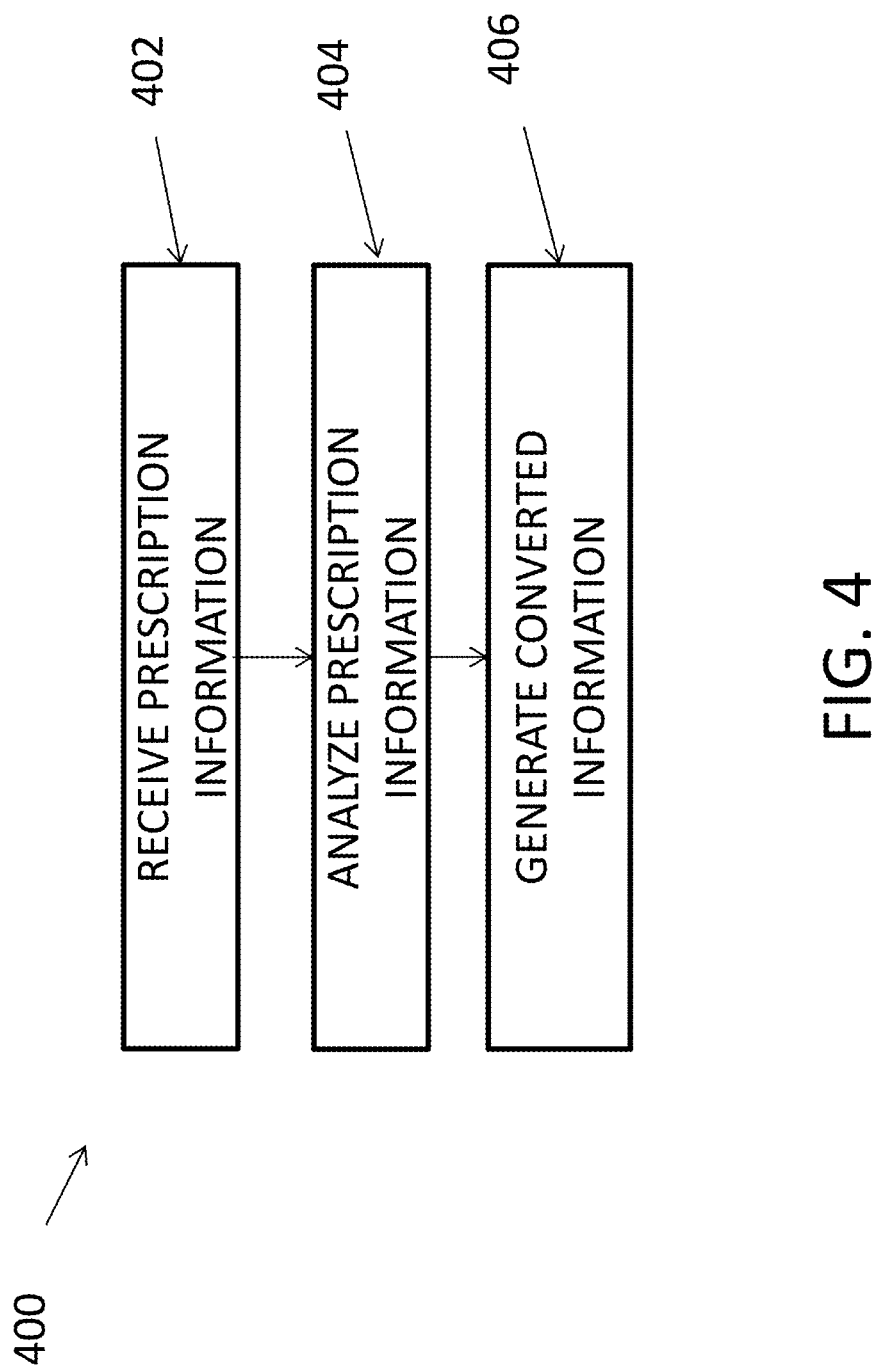
FIGS. 4 and 5 are flow diagrams of example electronic analysis of text.

FIG. 4 is a flow chart of an example process 400 for converting handwritten and/or printed information into converted text. In embodiments, example process 400 may be performed by electronic application 116, user device 112, and/or server 118. At step 402, user device 112 and/or electronic application 116 may receive prescription information. In embodiments, the prescription information may include a doctor's name, medical license information, doctor's address and phone number, patient's name, a date, medicinal information, doctor's signature, and a prescription number. In embodiments, the prescription information may be all handwritten, all printed, or partly handwritten and partly printed. In embodiments, user device 112 and/or electronic application 116 may receive the information in the prescription by the prescription first having being converted into an electronic format (e.g., jpeg format, PDF format, etc.) via an image capturing device such as a camera or scanning device that converts the non-electronic prescription document into an electronic format. In embodiments, the image capturing device may be a part of user device 116 or the image capturing device may be a separate device in communication with user device 116. In embodiments, an individual, such as a pharmacist, may electronically input symbols, texts, and/or letters onto the converted electronic format prior to the analysis of the document in the converted electronic format. In embodiments, an individual, such as a pharmacist, may handwrite write symbols, numbers, and/or letters onto the original document converted which is then converted to electronic format. Accordingly, the user device 112 and/or electronic application 116 may analyze the additional handwriting in addition to the text provided in the original document.

At step 404, user device 112 and/or electronic application 116 may analyze the prescription information. In embodiments, the analysis may analyze a doctor's name, doctor's address and phone number, doctor license information, patient's name, a date, medicinal information, doctor's signature, and a prescription number. In embodiments, the analysis also includes comparing the prescription information with stored information from previous prescriptions. In embodiments, the stored information may include information about particular medical professionals (such as doctors) and their handwriting styles. In embodiments, the prescription information may include non-handwritten text (e.g., computer generated text). In such embodiments, user device 112 and/or electronic application 116 may analyze the non-handwritten text for any errors, such as spelling mistakes, missing information, or incorrect written information. In embodiments, an individual may handwrite onto the prescription and the handwritten information may be analyzed along with the printed information on the electronic version of the prescription, i.e., the original document. In alternate embodiments, an individual may electronically enter information or change information onto the electronic version of the prescription.

In embodiments, the stored information may also include geographic information, time information, and spatial information associated with previous prescriptions. At step 406, user device 112 and/or electronic application 116 may generate a converted document. In embodiments, the converted document may include printed information of the handwritten information provided in the prescription. In embodiments, the printed information may have the same spatial relationship on the converted document as the original (prescription) document. In alternate embodiments, the printed information may have a different spatial relationship on the converted document versus the original (prescription) document. For example, two groups of information may be on the same line. User device 112 and/or electronic application 116 may change the position of the two groups so that each group is on a separate line. Alternatively, two groups of information may be on different lines. User device 112 and/or electronic application 116 may change the position of the two groups so that each group is on a separate line. In embodiments, the converted document may be further electronically changed based on electronic inputs into user device 112 and/or electronic application 116. For example, a pharmacist may analyze the converted document and change the converted document electronically via electronic inputs and/or handwritten information (which is then converted electronically) through user device 112 and/or electronic application 116.

Figure 5:
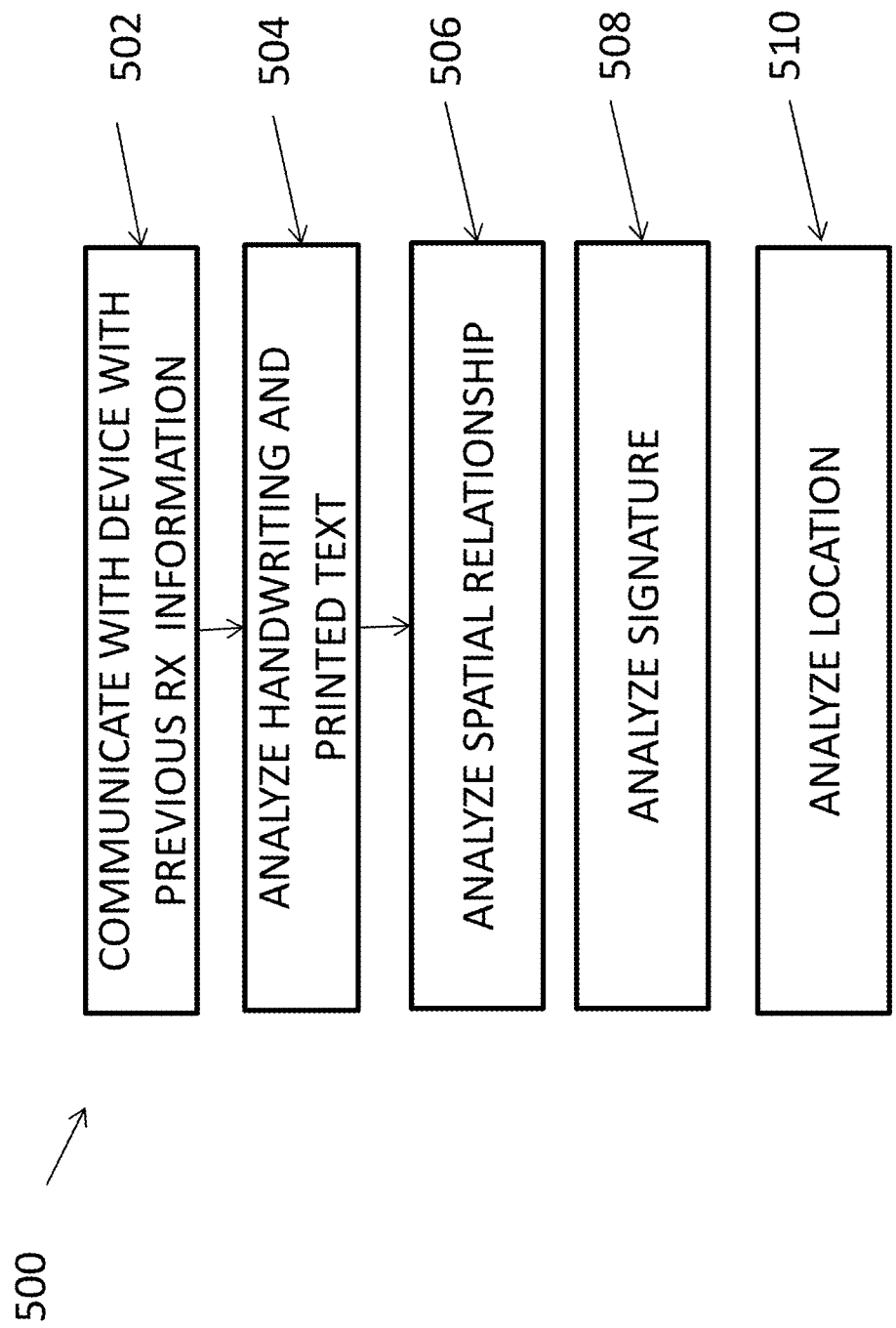

FIG. 5 is a flow chart of an example process 500 for analyzing information. In embodiments, the information may be printed and handwritten information on a prescription. In embodiments, example process 500 may be performed by electronic application 116 and/or user device 112. At step 502, user device 112 and/or electronic application 116 may communicate with another device (or multiple devices) that stores previous prescription information. In embodiments, the other device may be a server (e.g., server 118) or user device 114. In embodiments, the other device may communicate with user device 112 (and/or electronic application 116) via network 110 as described in FIG. 2. In embodiments, user device 112 and/or electronic application 116 may have access to one or more databases of past prescription information. In embodiments, the one or more databases may be similar to example data structure 600 as described in FIG. 6.

At step 504, user device 112 and/or electronic application 116 may analyze handwriting and/or printed text (e.g., words, numbers, and/or symbols) in the prescription. In embodiments, user device 112 and/or electronic application 116 may analyze every letter in a word or may analyze a portion of a word (e.g., penicillin may only "penic" and/or "lin" analyzed). In embodiments, the handwriting may be any size or any type of writing style. In embodiments, each handwritten letter, number, or symbol, is analyzed for the style of the handwriting. For example, a particular doctor may write "XYZ" with a particular style and also a particular amount of spacing between each letter. For example, that particular doctor may write "XYZ" with less than 0.1 cm spacing between each letter while another doctor may write "XYZ" with less than 0.1 cm spacing between the first two letters and greater than 0.1 cm spacing between the second and third letters. In embodiments, handwritten words may include letters that are joint to each other and have no space that is provided between the letters.

In embodiments, user device 112 and/or electronic application 116 may determine which letters, words, and/or symbols are printed and which letters, words, and/or symbols are handwritten. In embodiments, user device 112 and/or electronic application 116 may determine that letters, numbers, and/or symbols at certain locations on the prescription are printed rather than handwritten letters, numbers, and/or symbols. In embodiments, user device 112 and/or electronic application 116 may determine that the curvatures and lines indicate printed letters, numbers, and/or symbols. In embodiments, user device 112 and/or electronic application 116 may analyze each letter's, number's, and/or symbol's curvatures and lines. In embodiments, user device 112 and/or electronic application 116 may analyze the curvatures and lines separately and also analyze the relationship between curvatures and lines that make up a letter, number, and/or symbol. In embodiments, user device 112 and/or electronic application 116 may analyze broken lines within a letter, number, and/or symbol. In embodiments, user device 112 and/or electronic application 116 may analyze distance between handwritten and printed text. In embodiments, user device 112 and/or electronic application 116 may analyze whether letters are capitalized. In embodiments, user device 112 and/or electronic application 116 may analyze words, letters, numbers, and/or symbols that are joined together or that are separate. In embodiments, the words, letters, numbers, and/or symbols may be located on any location within the document. In embodiments, user device 112 and/or electronic application 116 may analyze the size of letters, numbers, and/or symbols. In embodiments, any of the features, shapes, lines, curves, and/or sizes of handwritten words, texts, and/or symbols is compared to information obtained from handwritten information from previous prescriptions stored by server 118. In embodiments, user device 112 and/or electronic application 116 may analyze spelling mistakes in the handwritten and the printed text. In embodiments, user device 112 and/or electronic application 116 may determine, if spelling mistakes exist, what is written in the handwritten and the printed text based on prior prescriptions, based on other text within a group or fragment, and/or based on the letters within the misspelled word.

At step 506, user device 112 and/or electronic application 116 may analyze the spatial relationship between different groupings of words, numbers, and/or symbols. In embodiments, user device 112 and/or electronic application 116 may determine a group. In embodiments, any grouping of words, numbers, and/or symbols may be written or printed on any area of the form (e.g., prescription). Accordingly, it is not necessary that any text, group of text, and/or a fragment of text be located in a pre-determined and/or specific location within the document for the text, group of text, and/or fragment of text to be analyzed. In embodiments, user device 112 and/or electronic application 116 may determine a fragment of a group. In embodiments, user device 112 and/or electronic application 116 may determine a group to be a particular number of combined letters, numbers, and/or words. In embodiments, a group may be a drug name and the size of one dosage of that particular drug. Thus, for example, if a drug is called ABC and the size of one dose of ABC is 100 mg, then a group may be "ABC 100 mg." In embodiments, a group may be just the drug name and the size of one dosage may be another group. Also, for example, "ABC" may be its own group and "100 mg" may be its own group. An example fragment may be "mg" of "100 mg." In embodiments, groups may be based on electronic analysis of the space between texts, symbols, and/or numbers. In embodiments, if the space is less than a particular threshold, then user device 112 and/or electronic application 116 may determine that the letters, numbers, and/or symbols are part of one group. For example, if the threshold is 0.1 inches, then any text, numbers, and/or symbols that are less than 0.1 inches are analyzed as one group. In embodiments, if the space is greater than a particular threshold, then the letters, numbers, and/or symbols are considered as separate groups. In embodiments, a second threshold may determine whether a group is constructed of multiple fragments. In embodiments, fragments may be determined by a space threshold or may be determined based on a combination of space and whether the letters, numbers, and/or symbols phonetically generate a particular word. For example, if a doctor has written "milligrams" in handwritten form, user device 112 and/or electronic application 116 may determine that "milli" and "grams" are fragments since they make dictionary-based words. Thus, in embodiments, user device 112 and/or electronic application 116 may have access to dictionaries.

In embodiments, user device 112 and/or electronic application 116 may analyze the spatial relationship by analyzing one group's relationship to another group as to whether the two groups are on the same line or the groups are on different lines. In embodiments, user device 112 and/or electronic application 116 may analyze different groups and assign their relationship based on whether they are horizontal, vertical or diagonal to other groups. In embodiments, user device 112 and/or electronic application 116 may analyze each group in comparison to another group based on a compass direction (e.g., northwest, south-south-west). In embodiments, user device 112 and/or electronic application 116 may analyze groups' spatial location to another group based on degrees and/or being clockwise or counter clockwise with a designated point as being 0 degrees. For example, group 1 may be 20 degrees clockwise from group 2.

In embodiments, user device 112 and/or electronic application 116 may analyze each group with another group based on a designated point within the group. In embodiments, the designated point may be at one of the endpoints of the group and/or at the center of the group. In alternate embodiments, the designated point may be a designated point that is independent of any group. Thus, each group's spatial relationship is based on the independent designated point (i.e., a particular position). In embodiments, the designated points may be based on a point with each group rather than a specified point on the document. Accordingly, in embodiments, user device 112 and/or electronic application 116 may determine one or more points within a group (e.g., center point, end points, etc.) and use those points in comparison to points in other groups to other their relationships.

At step 508, user device 112 and/or electronic application 116 may analyze a signature on the prescription. In embodiments, analysis of the signature may determine which doctor has written the prescription based on previous handwriting information stored by server 118 and/or other computing devices. For example, user device 112 and/or electronic application 116 may use the signature to determine that a particular doctor has written the prescription; and, based on determining the particular doctor, user device 112 and/or electronic application 116 may determine which handwriting style to use to analyze the handwritten letters, numbers, and/or symbols. In embodiments, if a doctor is writing a prescription for the first time, then user device 112 and/or electronic application 116 may not be able to use extracted information from previous prescriptions. Instead, user device 112 and/or electronic application 116 may analyze extracted information from one or more previous prescriptions to determine the handwritten letters, numbers, and/or symbols based on commonality. Alternatively, even if a doctor has written previous prescriptions, user device 112 and/or electronic application 116 may still use other handwriting styles to determine the handwritten text. Thus, multiple handwriting styles may be used to analyze handwriting even if one particular handwriting style has been confirmed.

At step 510, user device 112 and/or electronic application 116 may analyze location information provided in the prescription. In embodiments, location information may be the location of a doctor who has written the prescription. In embodiments, the location information may be printed or handwritten information. For example, the location information may be Miami, Fla. In embodiments, user device 112 and/or electronic application 116 may use the location information to determine and/or confirm a particular doctor's handwriting style. For example, a prescription may have information about a particular medical practice which the doctor is a part of. The doctor may also be involved with a hospital that is in an adjacent county or type of municipality. For example, the doctor may work at Broward General in Pembroke Pines, Fla. and also be part of a medical practice in Hialeah, Fla. Pembroke Pines is in Broward County while Hialeah is in Miami-Dade County. In this non-limiting example, user device 112 and/or electronic application 116 may determine that the prescription is from the practice in Hialeah, Fla. and analyze extracted information from one or more previous prescriptions from surrounding counties, such as Broward. Accordingly, if printed information about a particular doctor is not provided, location information may be used. Additionally, or alternatively, location information may be used to further confirm the identity of a medical professional who wrote the prescription. In embodiments, at steps 504, 506, 508, and/or 510, may electronically learn based on the information in the prescription and use that information to determine information written in future prescriptions.

FIG. 6 describes an example data structure 600 that stores electronic information associated with multiple prescriptions. In embodiments, data structure 600 may include a collection of fields such as ID 602, Location 604, Handwriting Style 606, Doctor 608, and Text 610. Although FIG. 6 shows example fields 602-610, in other embodiments, data structure 600 may include fewer fields, different fields, additional fields, and/or differently arranged fields than depicted in FIG. 6. In embodiments, user device 112 and/or electronic application 116 may store some or all of data structure 600. Additionally, or alternatively, server 118 and/or another computing device may store some or all of data structure 600. In embodiments, the information stored in example data structure 600 may be based on previously written prescriptions which are then used to analyze handwritten and/or non-handwritten text in future written prescriptions.

In embodiments, ID 602 may store information about particular identifiers for different handwriting styles used by doctors when writing prescriptions. In embodiments, ID 602 may be an alpha-numeric identifier. In embodiments, Location 604 may include information for a particular location associated with a doctor. In embodiments, Handwriting Style 606 may include analysis information for a particular handwriting style which is then given its own identifier. In embodiments, the identifier may classify particular traits associated with the particular handwriting style. In a non-limiting example, "C" in an identifier may indicate a handwriting style which is cursive. In another non-limiting example, "S" in an identifier may indicate a handwriting style where curvature of written letters is a characteristic. In another non-limiting example, "U" may indicate a handwriting style where the letters are written smaller than 8 font associated with a word processing software program. In embodiments, Handwriting Style 606 may include stored handwriting text from previous prescriptions. In embodiments, Doctor 608 may indicate a name of a doctor associated with a particular handwriting style. In embodiments, the identifier stored by Doctor 608 may include a surname. In alternate embodiments, the identifier stored by Doctor 608 may include a first name, first initial, and/or any other information. In embodiments, Text 610 may indicate identifiers that are associated with converted text based on handwritten text stored in Handwriting Style 606. In embodiments, Text 610 may indicate other identifiers that are associated with printed text from other prescriptions. In embodiments, user device 112 and/or electronic application 116 may determine and/or correct spelling mistakes and/or missing information based on previous printed text stored in Text 610. In embodiments, any information in ID 602, Location 604, Handwriting Style 606, Doctor 608, and/or Text 610 may require electronic verification prior to being used to determine future errors and/or to correct future errors in other prescriptions. Thus, an electronic communication that includes a pharmacist's identity, state license, and/or any other certification may be electronically included within any field within data structure 600 as used by user device 112 and/or electronic application 116.

Figure 7A:
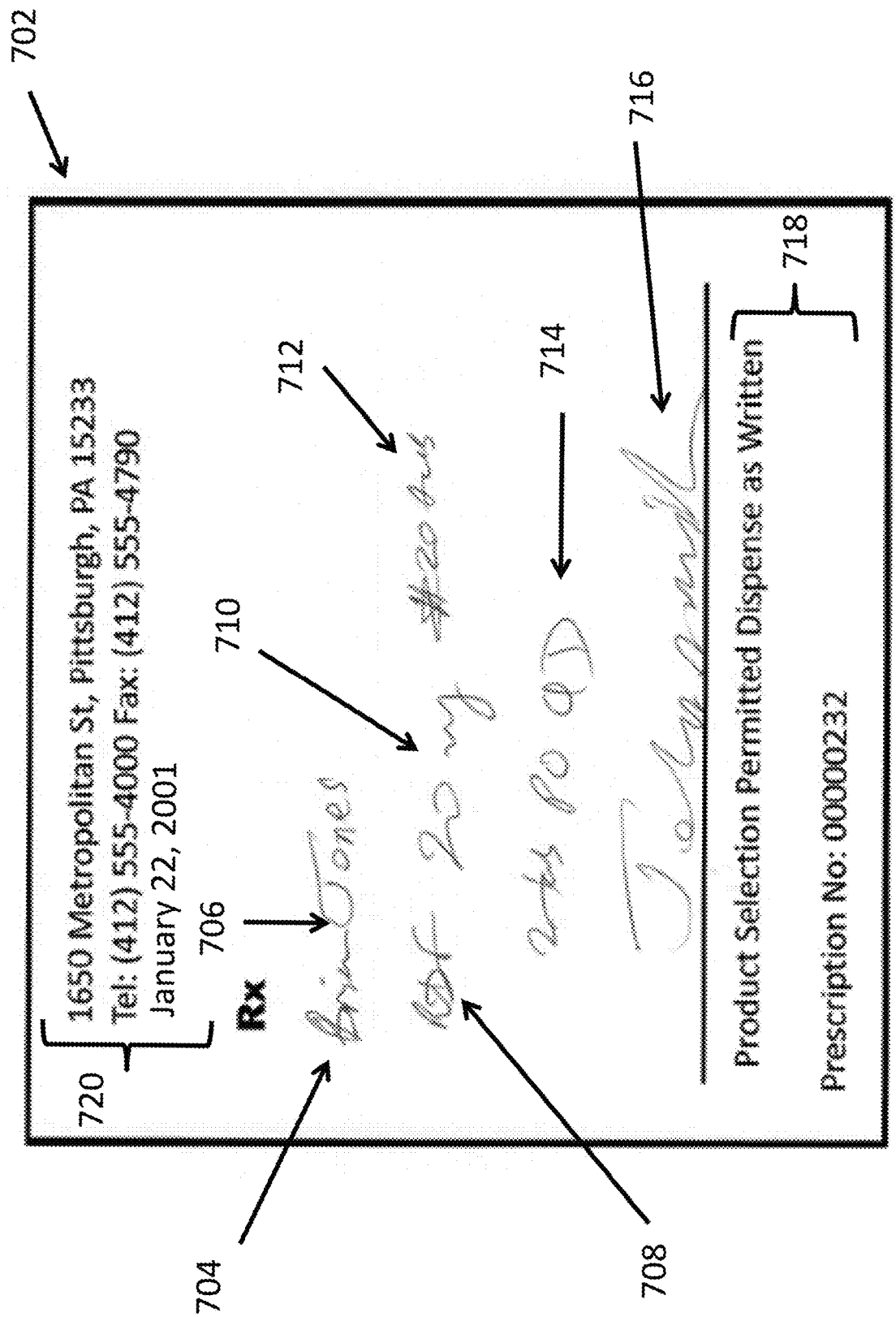
FIGS. 7A-7B, 8A-8B, 9A-9B, and 10A-10B are example electronic analyses of text.
Figure 7B:
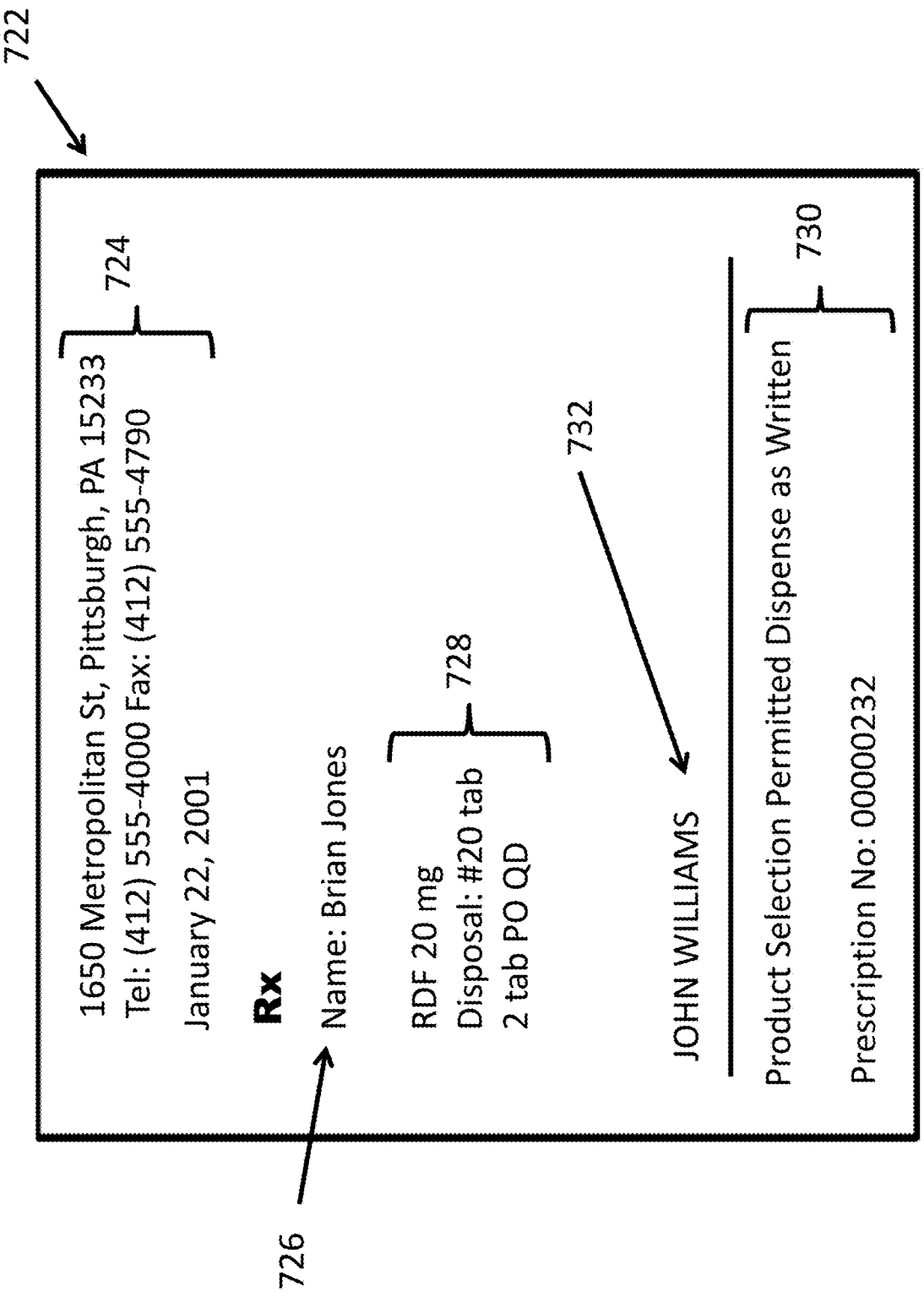

FIGS. 7A-7B is an example electronic analysis of text in a prescription. As shown in FIG. 7A, prescription 702 includes both printed and handwritten text. In this example, user device 112 and/or electronic application 116 conduct the analysis and do so by determining groups. In this example, the groups include patient name 704, medication 708, drug strength 710, tablet quantity 712, prescription directions 714, signature 716, printed information 718 and address 720. User device 112 and/or electronic application 116 analyze signature 716 and address 720 to determine the doctor who wrote the prescription. In other examples, the prescription may include the doctor's medical licensure number which can also be retrieved. Once the doctor is determined, a particular handwriting style is found along with associated printed information with that handwriting style. User device 112 and/or electronic application 116 then analyze the other groups. For patient name 704, the name is determined but the information extracted from the prescription is never stored (e.g., in a data structure 600). As shown in FIG. 7A, the handwritten name does not have a space between the first name and the last name. User device 112 and/or electronic application 116 determines that space 706 should exist based on determining that the Brian is a first name and that "BrianJones" is not a first name.

For medication 708, user device 112 and/or electronic application 116 may determine that the handwritten words are RDF based on previous handwritten words and associated printed letters in a database. Similarly, user device 112 and/or electronic application 116 also determines what the handwritten words provided in the groups of drug strength 710, tablet quantity 712, and prescription directions 714.

As shown in FIG. 7B, converted document 722 shows printed converted information based on the handwritten and printed information in prescription 702. As shown, converted document 722 includes address 724, name 726, medication information 728, prescription number 730, and doctor 732. In this example, the handwritten information and the converted information is also stored in a data structure (e.g., data structure 600) and is used for analysis of future handwritten prescriptions by electronic application 116. The patient's name is not stored in any data structure once the handwritten text has been analyzed and converted.

Figure 8A:
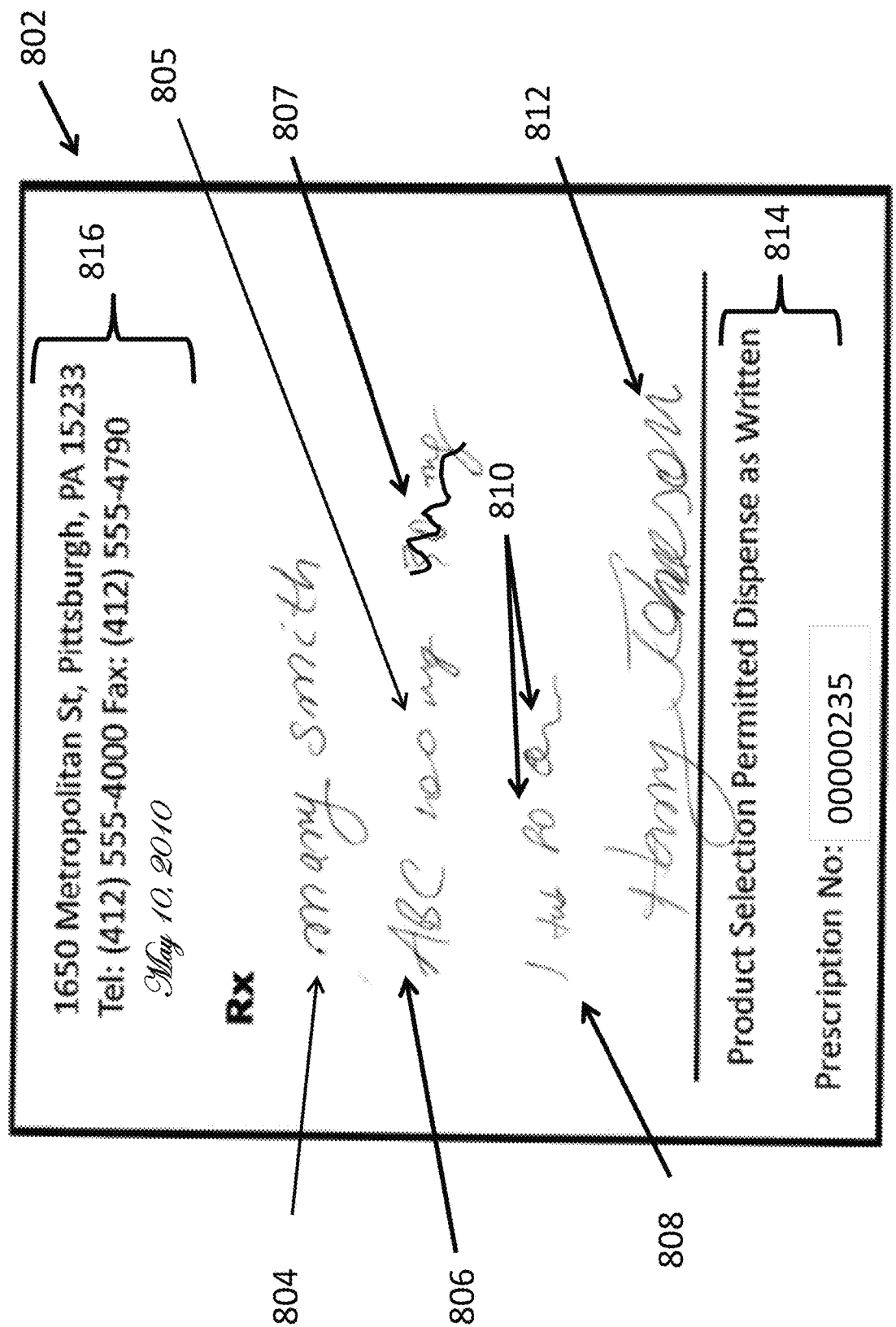
Figure 8B:
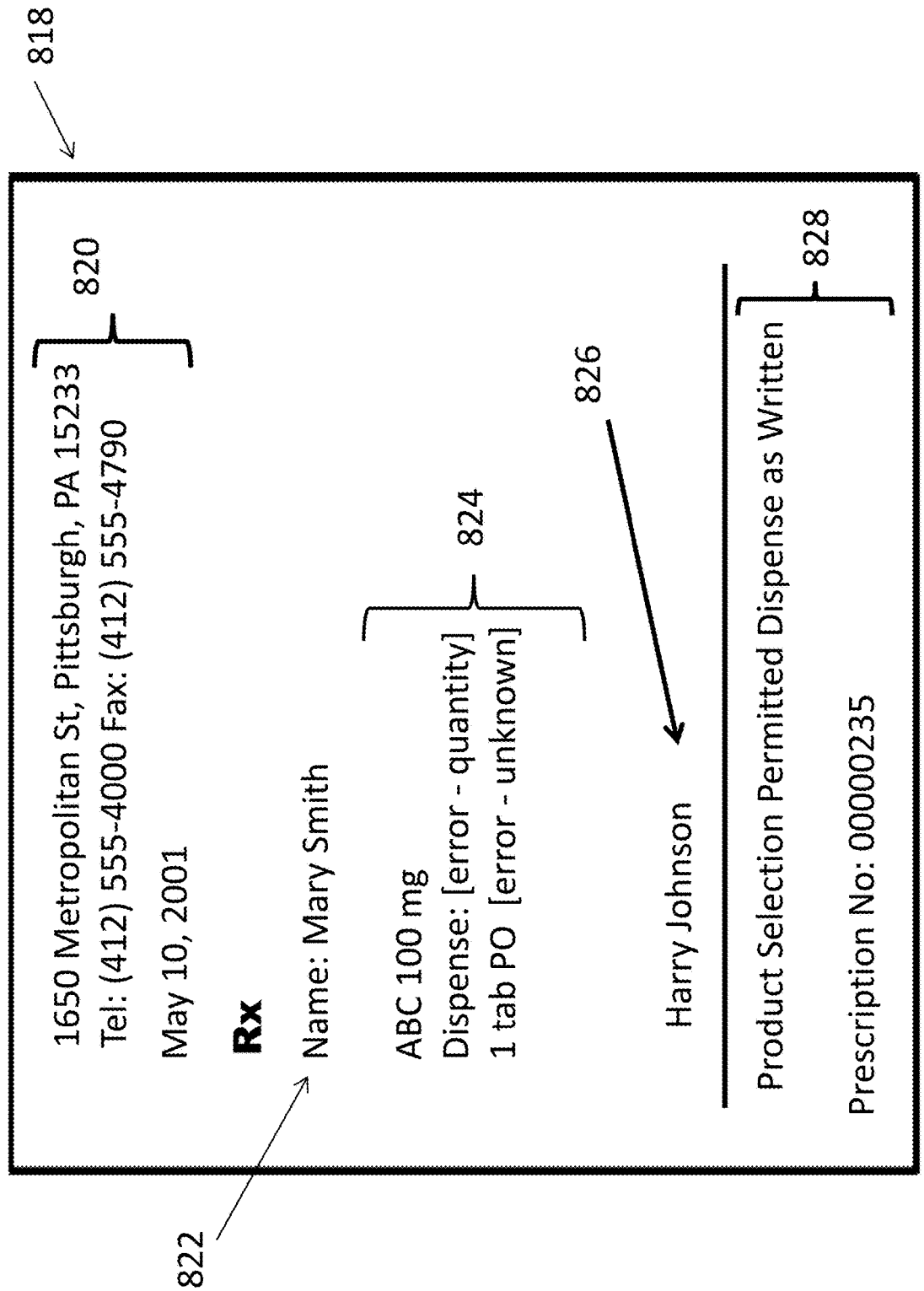

FIGS. 8A-8B is an example electronic analysis of text in a prescription. As shown in FIG. 8A, prescription 802 has been written by Dr. Harry Johnson. As further shown, prescription 802 includes patient name 804, drug 806, dosage 808, directions 810, doctor's signature 812, prescription number 814, and address/date 816. Once the doctor is determined, a particular handwriting style is found along with associated printed information with that handwriting style. User device 112 and/or electronic application 116 then analyze the other groups. For patient name 804, the name is determined but the patient identifying information extracted from the prescription is never stored (e.g., in a data structure 600). For drug 806, user device 112 and/or electronic application 116 determines the drug name based on previous prescriptions written by Dr. Harry Johnson. In addition, dosage 808 is also determined based on previous prescriptions written by Dr. Harry Johnson. Additionally, scribble 807 is also analyzed. Based on the form of the scribbles (including shape, length, and number of shapes) indicates that scribble 807 is not to be included in the prescription. Furthermore, user device 112 and/or electronic application 116 may determine since drug strength 805, dosage 808, and directions 810 already includes drug strength, dose and directions, the scribble shape of scribble 807 is not to be added to the converted document. Additionally, or alternatively, user device 112 and/or electronic application 116 may determine that since drug 806 and drug strength 805 is present, the scribble shape of scribble 807 is not to be added to the converted document and the drug and drug strength information is correct. In other examples, a doctor may, before the document is generated in electronic form, make handwritten corrections, and/or a pharmacist may also make corrections before the document is generated in electronic form. Such corrections may be then electronically analyzed (once the document is in electronic form) by user device 112 and/or electronic application 116 and used to anticipate future prescriptions with the same or similar mistakes and make or suggest corrections.

With dosage 808, user device 112 and/or electronic application 116 determines that the handwriting indicates 1 tablet. However, only a portion of the directions 810 are determined as PO, the remaining portion of directions 810 cannot be determined and is left as an unknown symbol/text. As shown in FIG. 8B, converted document 818 includes address 820, patient 822, medication 824, doctor 826, and prescription number 828. As shown in FIG. 8B, medication 824 includes some printed information that was derived from prescription 802 but with information not interpreted, the word "error" is given. For example, the dispensed quantity is not provided. In its place, "error" is given. Also, the complete directions were not determined from the handwriting and "error" is also given in its place. In this example, the handwritten information and the converted information is also stored in a data structure (e.g., data structure 600) and is used for analysis of future handwritten prescriptions by electronic application 116. The patient's name is not stored in any data structure once the handwritten text has been analyzed and converted.

In other examples, user device 112 and/or electronic application 116 may allow a pharmacist to enter a strikethrough line that is electronically generated and placed through portions of the prescription that should not be added to the converted documents. For example, the pharmacist may, using user device 112 and/or electronic application 116 enter a strikethrough line over "Tkea," so that "Theft" is now graphically shown. As a result "Theca" may not be included in the converted document. Also, if the strikethrough portion is part of a group of words, user device 112 and/or electronic application 116 may determine strikethrough portion based on the rest of the words in the group. For example, "Tkea 1 tablet PO QD" will be interpreted as "Take 1 tablet PO QD" based on "Tk-ea" being interpreted as "Take" based on the other words and letters in the group. Accordingly, user device 112 and/or electronic application 116 may exclude a portion of a group or a fragment based on the strikethrough feature or based on previous changes stored (e.g., such as by data structure 600). In embodiments, the strikethrough feature may change text within the group and/or fragment where the strikethrough feature is used within the same group and/or fragment that includes the changed text; or, strikethrough feature may change text within the group and/or fragment where the strikethrough feature is used within a different group. In embodiments, an error or mistake in the original document may be corrected by an individual (e.g., a pharmacist) by adding "Take" as a correction to the strikethrough. Accordingly, user device 112 and/or electronic application 116 may store errors and mistakes (and corrections) and generate suggestions (e.g., changes to a document) before an individual (such as a pharmacist) reviews similar documents in the future.

Figure 9A:
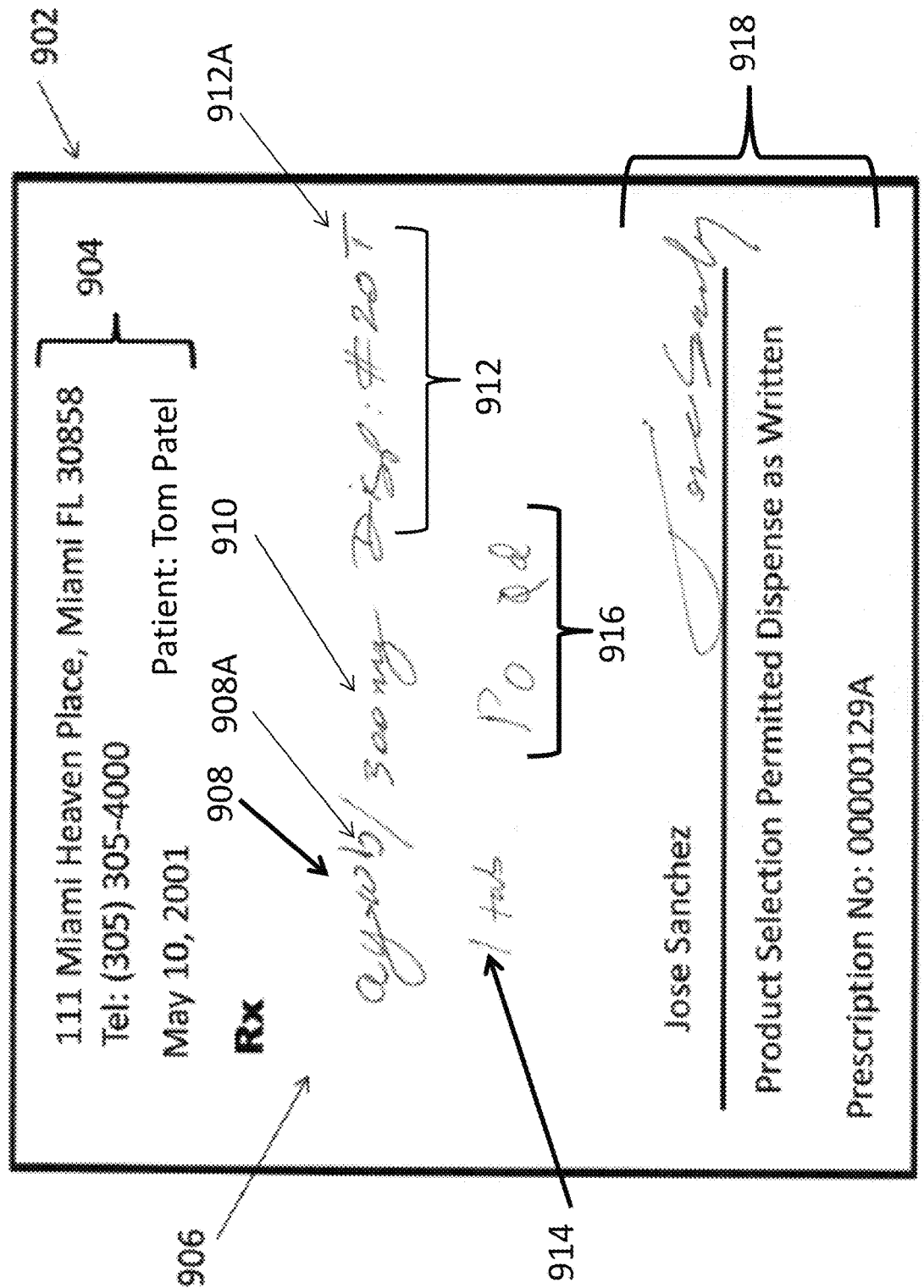
Figure 9B:
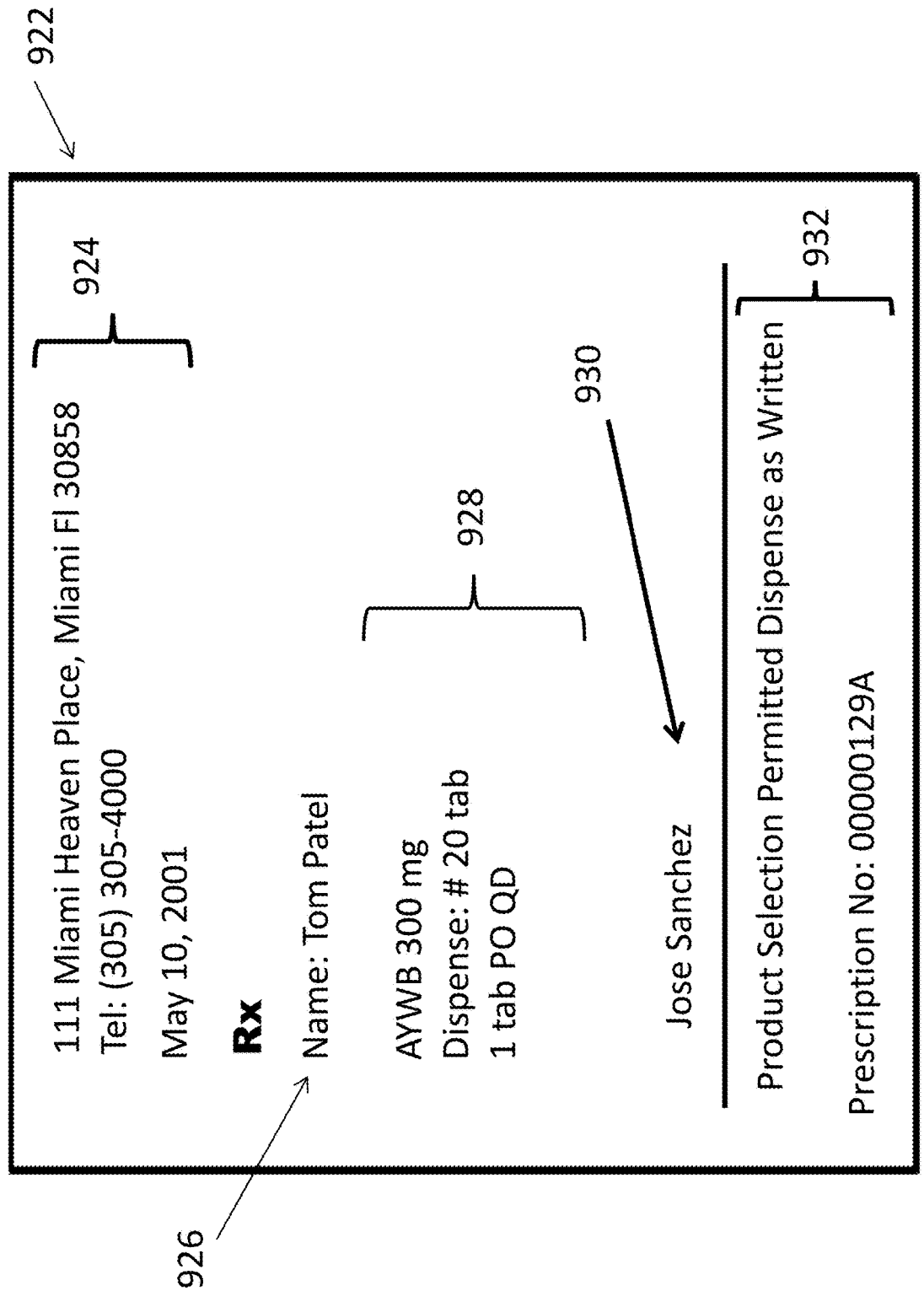

FIGS. 9A and 9B is an example electronic analysis in a prescription. As shown in FIG. 9A, Dr. Sanchez has written a prescription 902 for a patient, Tom Patel. As shown in FIG. 9A, prescription 902 includes doctor address and patient name 904, prescription space 906, drug 908, drug fragment 908A, drug strength 910, dispensed quantity 912, dispensed quantity fragment 912A, dosage 914, directions 916, doctor name and prescription number 918. User device 112 and/or electronic application 116 may analyze each of the groups and fragments shown in prescription 902. User device 112 and/or electronic application 116 may analyze doctor name and prescription number 918 and doctor address and patient name 904 to determine the doctor which then is used to find that doctor's handwriting style for analysis. In this example, electronic application 116 determines that Jose Sanchez is the doctor located in Miami, Fla. In doing so, electronic application 116 then analyzes the handwriting within prescription space 906. Electronic application 116 analyzes drug 908. Analyzing drug 908, electronic application 116 determines that the first three letters are "awy." Upon analyzing the rest of drug 908, electronic application 116 comes across drug fragment 908A which includes a letter. The letter is not a continuous line and includes a break within the lines.

Electronic application 116 determines, based on the doctor's past prescriptions, that drug fragment 908A is the letter "b." Accordingly, electronic application 116 determines that the drug is "awyb." Electronic application 116 also determines that dosage 910 is "300 mg." For dispensed quantity 912, dispensed quantity fragment 912A indicates "T." Electronic application 116 determines that "T" is for "tablet" based on Dr. Sanchez's past handwriting information. Electronic application 116 determines that dosage 914 is one tablet and directions 916 are interpreted as "PO QD" which is defined as "by mouth every day" resulting in the directions reading "Take one tablet by mouth every day".

FIG. 9B shows converted document 922 which is based on electronic application 116's analysis of prescription 902 as described in FIG. 9A. As shown in FIG. 9B, converted document 922 includes doctor's address and date 924, patient name 926, drug prescription 928, doctor 930, and prescription number 932. As shown in FIG. 9B, electronic application 116 has moved the location of the dispensed quantity information below the drug information so that the dispensed quantity information and the drug information are on separate lines. This is in contrast to prescription 902 which has the drug information and the dispensed quantity information on the same line. In this example, the handwritten information and the converted information is also stored in a data structure (e.g., data structure 600) and is used for analysis of future handwritten prescriptions by electronic application 116. The patient's name is not stored in any data structure once the handwritten text has been analyzed and converted.

Figure 10A:
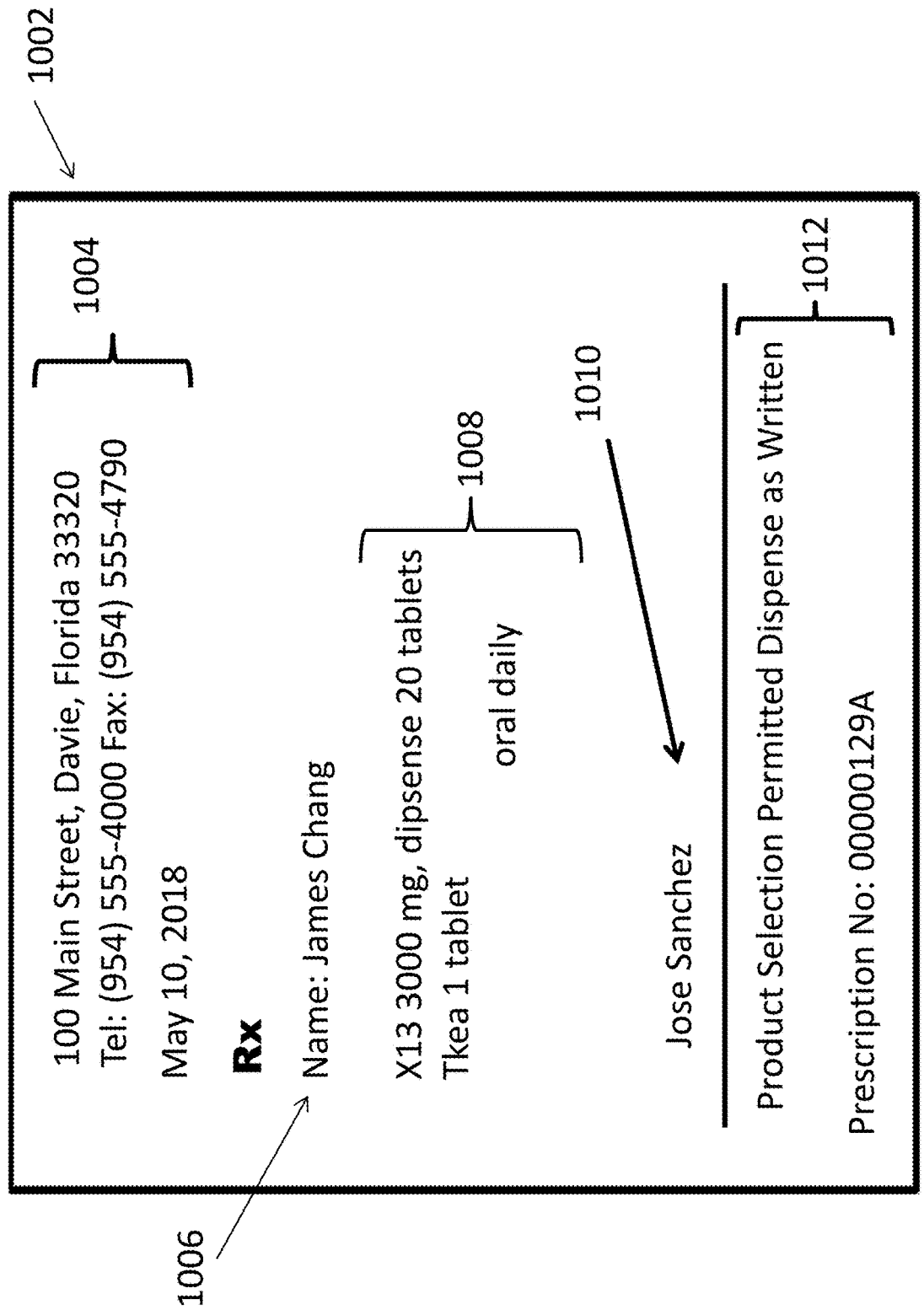
Figure 10B:
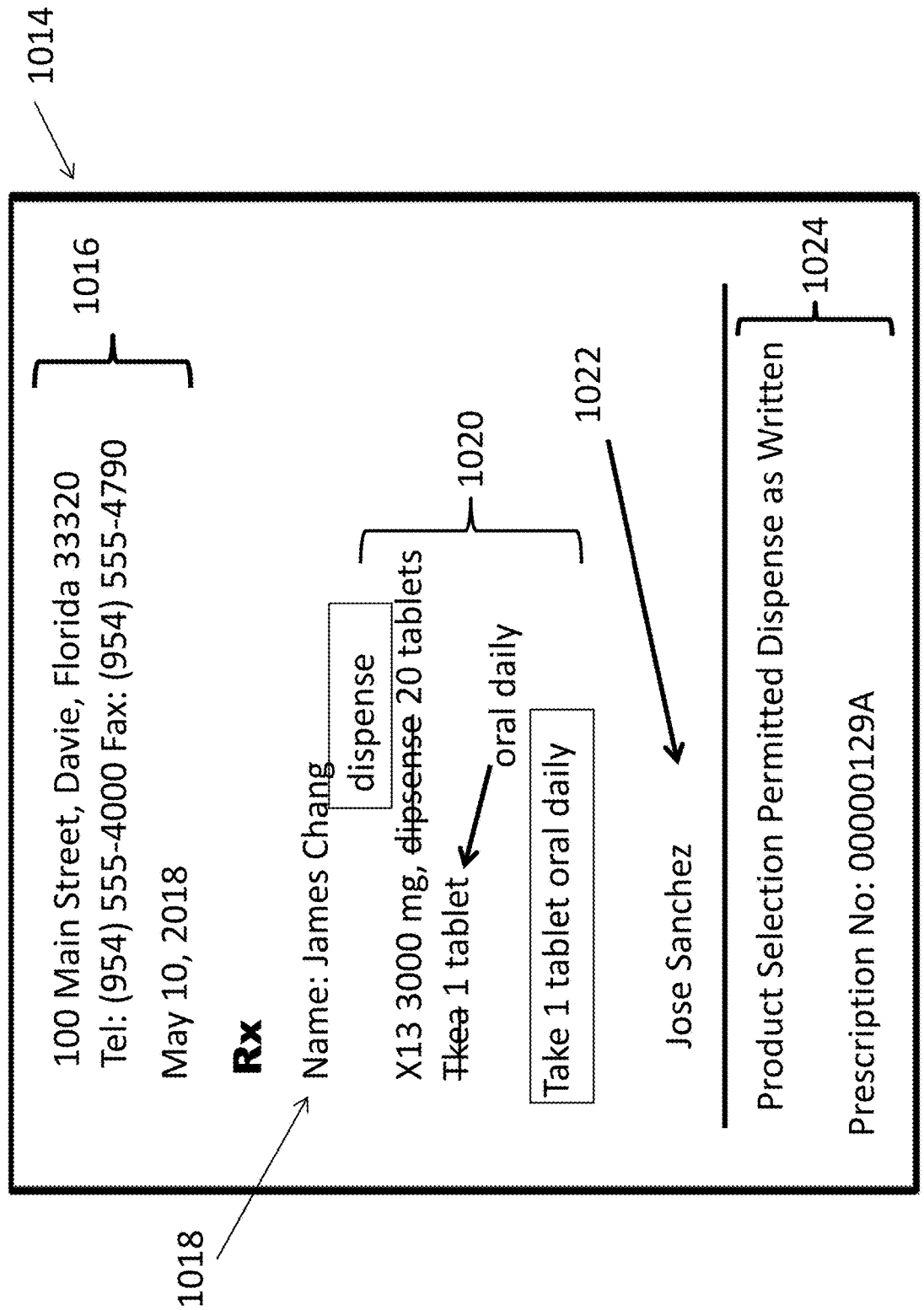

FIGS. 10A and 10B is an example of electronic analysis in a prescription. FIG. 10A shows an example prescription 1002. Unlike the examples in FIGS. 7A, 8A, and 9A, prescription 1002 is electronically generated by a doctor on an electronic form with all the information typed onto the electronic form being used as a prescription. Prescription 1002 includes address 1004, patient name 1006, dosage and usage information 1008, doctor signature 1010, prescription number 1012. In this example, one group is defined, dosage and usage information 1008, and includes all the dosage and usage information provided by the doctor for the patient's medication. As shown in FIG. 10A, the dosage and usage information 1008 has spelling mistakes. This includes a misspelling of "dispense" and "take." Based on previous prescription information issued by the same doctor, user device 112 and/or electronic application 116 may determine that "dispense" and "take" are misspelt. User device 112 and/or electronic application 116 may have stored information that indicates that in previous instances a pharmacist would make the correction and enter the correction which would then be used to learn about spelling mistakes made by a particular doctor. Accordingly, user device 112 and/or electronic application 116 may electronically analyze the past corrections electronically inputted and use those to determine future incorrect spellings in documents.

User device 112 and/or electronic application 116 may learn that particular words are misspelt if the number of misspelt words stored by user device 112, or another device, exceeds a particular threshold. In embodiments, threshold levels stored by user device 112 and/or electronic application 116 may be associated with different doctors and different types of spelling mistakes. Thus, misspelling of drug names has a lower threshold (e.g., requiring less instances for the device to learn to catch those mistakes) versus a misspelling in the doctor's or patient's address as printed on the prescription. User device 112 and/or electronic application 116 may also determine that "oral daily" should be on the same line as the "Take 1 tablet." Accordingly, user device 112 and/or electronic application 116 may correct the spelling mistakes also change the location of the "oral daily." As shown in FIG. 10B, converted prescription 1014 includes information from prescription 1002 (in FIG. 10A) and also includes correction information that was shown in FIG. 10A. As shown in FIG. 10B, converted prescription 1014 includes the errors shown in FIG. 10A along with the corrections. While not shown in FIG. 10B, an electronically generated stamp or signature may be generated and shown on converted prescription 1014 to indicate that the corrections were made and each user(s) who made and/or approved changes. Prior to the corrections being stored by user device 112 and/or electronic application 116, converted prescription 1014 may be electronically sent to a computing device used by the doctor who generated prescription 1002. Additionally, the corrections may be electronically communicated to a doctor for confirmation of the corrections.

In embodiments, FIGS. 7A, 7B, 8A, 8B, 9A, 9B, 10A, and 10C, electronic information may be provided to one data structure 600 or may be sent to multiple other data structures that are associated with different computing devices. For example, the electronic information may be sent to computing devices that are associated with the electronic verification of information for the electronic transfer of electronic tokens from one computing device to another computing device. Even though particular combinations of features are recited in the claims and/or disclosed in the specification, these combinations are not intended to limit the disclosure of the possible implementations. In fact, many of these features may be combined in ways not specifically recited in the claims and/or disclosed in the specification. Although each dependent claim listed below may directly depend on only one other claim, the disclosure of the possible implementations includes each dependent claim in combination with every other claim in the claim set.

While various actions are described as selecting, displaying, transferring, sending, receiving, generating, notifying, and storing, it will be understood that these example actions are occurring within an electronic computing and/or electronic networking environment and may require one or more computing devices, as described in FIG. 2, to complete such actions. Furthermore, it will be understood that these various actions can be performed by using a touch screen on a computing device (e.g., touching an icon, swiping a bar or icon), using a keyboard, a mouse, or any other process for electronically selecting an option displayed on a display screen to electronically communicate with other computing devices as described in FIG. 2. Also it will be understood that any of the various actions can result in any type of electronic information to be displayed in real-time and/or simultaneously on multiple user devices (e.g., similar to user device 116). For FIGS. 4 and 5, the order of the blocks may be modified in other implementations. Further, non-dependent blocks may be performed in parallel. Also, it will be understood that any electronic post may include information about services and other information that may include user-generated and non-user generated text, numbers, photos, animation, multimedia content, and/or any other type of electronic content that can be analyzed for any of the reasons described in the above figures.

No element, act, or instruction used in the present application should be construed as critical or essential unless explicitly described as such. Also, as used herein, the article "a" is intended to include one or more items and may be used interchangeably with "one or more." Where only one item is intended, the term "one" or similar language is used. Further, the phrase "based on" is intended to mean "based, at least in part, on" unless explicitly stated otherwise. Also, the phrase "converted text," or "converted information" may indicate information that has been converted from handwritten or non-handwritten information to printed information. The phrase "information" may indicate letters, words, numbers, and/or symbols. The phrase "text" may indicate letters, numbers, and/or symbols. The phrases "information" and "text" may indicate the same thing, i.e., letters, numbers, and/or symbols. Also, while the above examples are associated with prescriptions, pharmacists, and doctors, the above example actions may also be used for other scenarios and analysis of other types of handwritten text, such as with purchase orders, shipping orders, etc.

In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

What is claimed is:

1. An electronic communications method for electronically correcting prescription information, comprising:
   receiving, by a computing device, an electronic communication,
      the electronic communication including information,
         wherein the information includes a first set of graphics and a second set of graphics;
   analyzing, by the computing device, the first set of graphics and the second set of graphics simultaneously,
      wherein the analyzing the first set of graphics includes analyzing a first identifier and the analyzing the second set of graphics includes analyzing electronic data associated with prescription information;
      wherein the analyzing the electronic data includes analyzing curves, lengths, and shapes associated with the electronic data,
         wherein the shapes, the lengths, and the curves are converted into different shapes;
   determining, by the computing device, the shapes, the lengths, and the curves are associated with the first identifier;
   determining, by the computing device, that the information has a spelling mistake based on associating the shapes, the lengths, and the curves with the first identifier; and
   generating, by the computing device, updated electronic text in a converted document based on analyzing the handwritten text, wherein the computing device electronically corrects the spelling mistake by generating a converted document with the updated electronic text associated with one or more words that are different provided in the information.

2. The electronic communications method of claim 1, where the generating the updated electronic text does not include one of more curves associated with the electronic data.

3. The electronic communications method of claim 1, wherein the information includes a third set of graphics, the electronic communications method further comprising:
   analyzing, by the computing device, the third set of graphics simultaneously with the first set of graphics or the second set of graphics;
   determining, by the computing device, the third set of graphics is located in a first distance from the first set of graphics;
   determining, by the computing device, that the first distance be changed so that the third set of graphics are located a second distance from the second set of graphics when the converted document is electronically displayed.

4. The electronic communications method of claim 3, where the third set of graphics is associated with a doctor's name.

5. The electronic communications method of claim 4, where the information includes a fourth set of graphics, wherein the fourth set of graphics is associated with patient address information.

6. The electronic communications method of claim 3, where the first set of graphics includes different quantities of fragments.

7. The electronic communications method of claim 4, where the analyzing the information, received in the electronic communication, includes determining a spatial relationship between text, wherein the first set of graphics are part of the text.

8. The electronic communications method of claim 6, where the converted document does not include any of the fragments.

9. The electronic communications method of claim 1, where electronic information is based on a non-electronic document.

10. The electronic communications method of claim 7, where the analysis of the electronic information includes analyzing geographic information.

11. The electronic communications method of claim 1, where:
   the information includes at least one of:
      drug name information,
      drug quantity information, and
      drug usage information.

12. A device, comprising:
   one or more processors to:
      electronically receive electronic information,
         the electronic information including a first set of graphics, a second set of graphics, and a third set of graphics;
      analyze, the electronic information,
         the analyzing includes simultaneously analyzing the first set of graphics,
      the second set of graphics, and the third set of graphics;
      determine a first relationship between the first set of graphics and the second set of graphics, wherein the analyzing includes, based on the first relationship, determining any errors in the second set of graphics is based on the first set of graphics;

determine, based on the particular analysis of the shapes in the second set of graphics, a spelling mistake in the electronic information;

generate printed text based on analyzing the first set of graphics, the second set of graphics, and the third set of graphics, wherein the printed text does not include the spelling mistake in the electronic information does include one or more correctly spelt words; and generate a converted document with the printed text based on the electronic information.

13. The device of claim 12, where the electronic information includes a fourth set of graphics, wherein the fourth set of graphics has a grammatical error, and the one or more processors are further to:

electronically remove the fourth set of graphics from being displayed in the converted document.

14. The device of claim 13, where the one or more correct spelt words in the converted document is based on analyzing previous documents.

15. The device of claim 14, where the electronic information is made up of multiple groups of text.

16. The device of claim 14, where each of the multiple groups of text consists of one of more fragments.

17. The device of claim 16, where the analyzing the electronic information includes the one or more processors to:

add electronic markings onto the electronic information; and analyze the electronic information based on the electronic markings.

18. The device of claim 17, where the analyzing the electronic information based on the electronic markings includes analyzing misspelt words within a group of the electronic information.

19. A non-transitory computer-readable medium storage instructions, the instructions comprising:

a plurality of instructions that, when executed by a processor of a device, cause the processor to:

receive electronic information,
wherein the electronic information includes a first set of graphics, a second set of graphics, and a third set of graphics,
the first set of graphics is associated with a doctor's name, the second set of graphics is associated with drug information, and the third set of graphics is associated with geographic information;

analyze the electronic information,
where the analyze the electronic information includes:
determine a first relationship between the first set of graphics and the second set of graphics, wherein the first relationship determines how the second set of graphics are to be analyzed, and
determine a second relationship between the first set of graphics and the third set of graphics, wherein the second relationship confirms a particular handwriting style of a particular doctor identified in the first set of graphics; the analyzing includes analyzing the handwritten text;

generate printed text based on analyzing the electronic information; and generate a converted document with the printed text based on the electronic information.

20. The non-transitory computer-readable medium of claim 19, comprising additional instructions, when executed by the processor of the device, cause the processor to further:

determine, based on the analysis of the second set of graphics, that the second set of graphics includes a word that is not a correctly spelt word; and remove the word that is not correctly spelt.

\* \* \* \* \*